US00PP25943P2

(12) United States Plant Patent
Jandrew

(10) Patent No.: US PP25,943 P2
(45) Date of Patent: Sep. 22, 2015

(54) ***PENTAS* PLANT NAMED 'PEZZ0001'**

(50) Latin Name: *Pentas lanceolata*
Varietal Denomination: PEZZ0001

(71) Applicant: Syngenta Crop Protection AG, Basel (CH)

(72) Inventor: Jason Jandrew, Nipomo, CA (US)

(73) Assignee: Syngenta Crop Protection AG, Basel (CH)

( * ) Notice: Subject to any disclaimer, the term of this patent is extended or adjusted under 35 U.S.C. 154(b) by 123 days.

(21) Appl. No.: 13/998,369

(22) Filed: Oct. 25, 2013

Related U.S. Application Data

(60) Provisional application No. 61/891,955, filed on Oct. 17, 2013.

(51) Int. Cl.
*A01H 5/02* (2006.01)

(52) U.S. Cl.
USPC ..... Plt./466

(58) Field of Classification Search
USPC ..... Plt./466
See application file for complete search history.

*Primary Examiner* — Susan McCormick Ewoldt
(74) *Attorney, Agent, or Firm* — Joshua L. Price

(57) ABSTRACT

A new *Pentas* plant named 'PEZZ0001' particularly distinguished by the large sized inflorescences with light purple colored flowers, dark yellow-green foliage, vigorous and upright habit with strong branches, and tolerates hot, summer conditions.

1 Drawing Sheet

Latin name of the genus and species of the plant claimed: *Pentas lanceolata.*

Varietal denomination: 'PEZZ0001'.

BACKGROUND OF THE NEW PLANT

The present invention comprises a new *Pentas,* botanically known as *Pentas lanceolata,* and hereinafter referred to by the variety name 'PEZZ0001'.

'PEZZ0001' is a product of a planned breeding program. The new cultivar 'PEZZ0001' has large sized inflorescences with light purple colored flowers, dark yellow-green foliage, vigorous and upright habit with strong branches, and tolerates hot, summer conditions.

'PEZZ0001' originates from a hybrid cross made in a breeding program in July 2006 in a greenhouse in Gilroy, Calif. The female parent was an unpatented, proprietary plant identified as 'T50A-4' with violet colored flowers. The male parent of 'PEZZ0001' was an unpatented, proprietary plant, identified as 'T7A-1' with white colored flowers. The resultant seed was sown in a greenhouse in January 2007.

'PEZZ0001' was selected as one flowering plant within the progeny of the stated cross in May 2007 in Gilroy, Calif.

The first act of asexual reproduction of 'PEZZ0001' was accomplished when vegetative cuttings were propagated from the initial selection in May 2007 in a greenhouse in Gilroy, Calif.

BRIEF SUMMARY OF INVENTION

Horticultural examination of plants grown from cuttings of the plant initiated in May 2007 in Gilroy, Calif., and continuing thereafter, has demonstrated that the combination of characteristics as herein disclosed for 'PEZZ0001' are firmly fixed and are retained through successive generations of asexual reproduction.

'PEZZ0001' has not been observed under all possible environmental conditions. The phenotype may vary significantly with variations in environment such as temperature, light intensity, and day length.

A Plant Breeder's Right for this cultivar was applied for in Canada on Nov. 2, 2012 (12-7778). 'PEZZ0001' has not been made publicly available more than one year prior to the filing of this application.

The following traits have been repeatedly observed and are determined to be basic characteristics of the new variety. The combination of these characteristics distinguishes this *Pentas* as a new and distinct variety.

BRIEF DESCRIPTION OF THE PHOTOGRAPHS

The accompanying photographic drawing shows typical flower and foliage characteristics of 'PEZZ0001' with colors being as true as possible with an illustration of this type.

The photographic drawing shows two flowering plants of the new variety growing in one container and a close-up of a flower.

DETAILED BOTANICAL DESCRIPTION

The plant descriptions, measurements and photographs were taken in Gilroy, Calif. in mid-April 2013 under natural light. These plants were approximately 16-18 weeks old and were grown two plants per one gallon container, in a greenhouse trial.

Color references are made to The Royal Horticultural Society Colour Chart (R.H.S.) 2001.

TABLE 1

DIFFERENCES BETWEEN THE NEW VARIETY 'PEZZ0001' AND A MOST SIMILAR VARIETY

| | 'PEZZ0001' | 'Bismarck Pink' (U.S. Plant Pat. No. 15,780) |
|---|---|---|
| Habit: | Much more vigorous | Less vigorous |
| Leaf size: | Larger | Smaller |
| Flower size/color: | Larger/light purple | Smaller/pink |

Plant:

*Form, growth and habit.*—Upright, sturdy and vigorous growth habit; good heat tolerance with continuous flowering through summer; well-branched plant habit.

*Plant height.*—19-20.0 cm.

*Plant height (inflorescence included).*—25-28.0 cm.

*Plant width.*—27-29.0 cm.

Roots:

*Number of days to initiate roots.*—12-14 days at about 22 degrees C.

*Number of days to produce a rooted cutting.*—4-5 weeks at 22 degrees C.

*Type.*—Fine, fibrous, free branching.

*Color.*—RHS N155B but whiter.

Foliage:

*Arrangement.*—Opposite.

*Immature leaf, color upper surface.*—Closest to RHS 147A; glossy.

*Immature leaf, color lower surface.*—Closest to RHS 147B.

*Mature leaf, color upper surface.*—Closest to RHS 147A.

*Mature leaf, color lower surface.*—Closest to RHS 147B.

*Length.*—8-11.0 cm.

*Width.*—4.5-5.3 cm.

*Shape.*—Ovate to slightly elliptical.

*Base shape.*—Attenuate.

*Apex shape.*—Acute.

*Margin.*—Entire.

*Texture upper side.*—Hirsute.

*Texture lower side.*—Hirsute and more heavily on the veins.

*Color of veins, upper surface.*—RHS 144C.

*Color of veins, lower surface.*—RHS 144C.

*Pattern of veining.*—Pinnate.

*Petiole color.*—RHS 144C.

*Petiole length.*—1.5-1.8 cm.

*Diameter of petiole.*—0.25 cm.

*Texture.*—Hirsute.

Stem:

*Quantity of branches.*—4-5.

*Color of stem.*—RHS 144A with some anthocyanins on the upper facing surface of light shades of RHS N200A.

*Length of stem.*—16-20.0 cm.

*Diameter.*—0.4-0.5 cm.

*Length of internodes.*—3.5-5.0 cm.

*Texture.*—Hirsute.

Peduncle:

*Color of peduncle.*—RHS 144B with a few blotches of RHS 144A.

*Length of peduncle.*—1-2.5 cm.

*Peduncle diameter.*—0.2 cm.

*Peduncle texture.*—Hirsute.

Pedicel:

*Color of pedicel.*—RHS 144C.

*Length of pedicel.*—0.2-0.3 cm.

*Diameter of pedicel.*—0.1 cm.

*Pedicel texture.*—Hirsute.

Bud (just before opening):

*Color.*—RHS 76D at the apex portion, with the tube being more RHS 75D.

*Length.*—2.7-2.9 cm.

*Width.*—0.4-0.5 cm.

*Shape.*—Oblong.

Inflorescence:

*Type.*—Terminal corymb; but more umbel looking.

*Natural flowering.*—Late spring and summer, flowers continuously.

*Number of inflorescences per plant.*—4 with open flowers and 2 immature with just buds.

*Fragrance.*—None.

*Inflorescence diameter.*—10-11.0 cm.

*Inflorescence depth.*—4.5-5.0 cm.

Corolla:

*Form.*—Single, tubular-shaped flowers consisting of a single whorl of 5 pointed petals fused at the base; aspect flat; very free flowering.

*Lastingness of individual flowers.*—About 3-4 weeks depending on temperature.

*Diameter of floret.*—2.3-2.4 cm.

*Depth of floret.*—3.3-3.5 cm.

*Immature.*—Color upper petals, upper surface: RHS76D overlaid with shades of RHS N74C leaving more RHS 76D at the margin. Color upper petals, lower surface: RHS 75C.

*Mature.*—Color upper petals, upper surface: Light shades of RHS 74C fading to shades of RHS 75C, RHS 75D and even RHS 76D. Color upper petals, lower surface: Closest to RHS 75D.

*Length petals.*—0.9-1.0 cm.

*Width of petals.*—0.6 cm.

*Petal shape.*—Broadly ovate.

*Apex shape.*—Almost cuspidate and pinched looking; some are a bit twisted to one side or the other.

*Margin.*—Entire.

*Base.*—Fused.

*Petal texture, upper surface.*—Papillose.

*Petal texture, lower surface.*—Papillose, with some hairs down the midvein.

*Corolla tube color, inside.*—RHS N155B with a hint if RHS 63D.

*Corolla tube color, outside.*—Closest to RHS 75C.

*Corolla tube length.*—1.9-2.0 cm.

*Corolla tube diameter.*—0.15 cm.

*Corolla tube texture, inside.*—Very hirsute at throat with hairs running the length of the tube.

*Corolla tube texture, outside.*—Hiruste.

*Corolla throat diameter.*—0.5 cm.

Calyx:

*Number of sepals.*—5.

*Color of sepals.*—Closest to RHS 147A.

*Length of sepals.*—0.8-0.9 cm.

*Width of sepals*.—0.15 cm.

*Sepal shape*.—Lanceolate.

*Apex shape*.—Acute.

*Margins*.—Entire, where not fused.

*Texture, upper surface*.—Glabrous, with hairs at the margins.

*Texture, lower surface*.—Hirsute.

Reproductive organs:

*Gynoecium*.—Pistil: 1. Length: 2.0. Style color: RHS 155C. Style length: 2.0 cm. Stigma color: Closest to RHS 59B with a little more grey. Sigma type: Bi-parted; pubescent. Ovary color: RHS N144A. Ovary length: 0.1 cm. Ovary diameter: 0.1 cm.

*Androecium*.—Number of stamens: 5, with filaments fused to the corolla wall. Anther color: RHS 197B. Length of anthers: 0.2 cm. Color of pollen: RHS 155A. Pollen amount: Less than normal.

Fertility/seed set: Has not been determined to date.

Disease/pest resistance: Has not been determined to date.

What is claimed is:

1. A new and distinct variety of *Pentas* plant named 'PEZZ0001' substantially as illustrated and described herein.

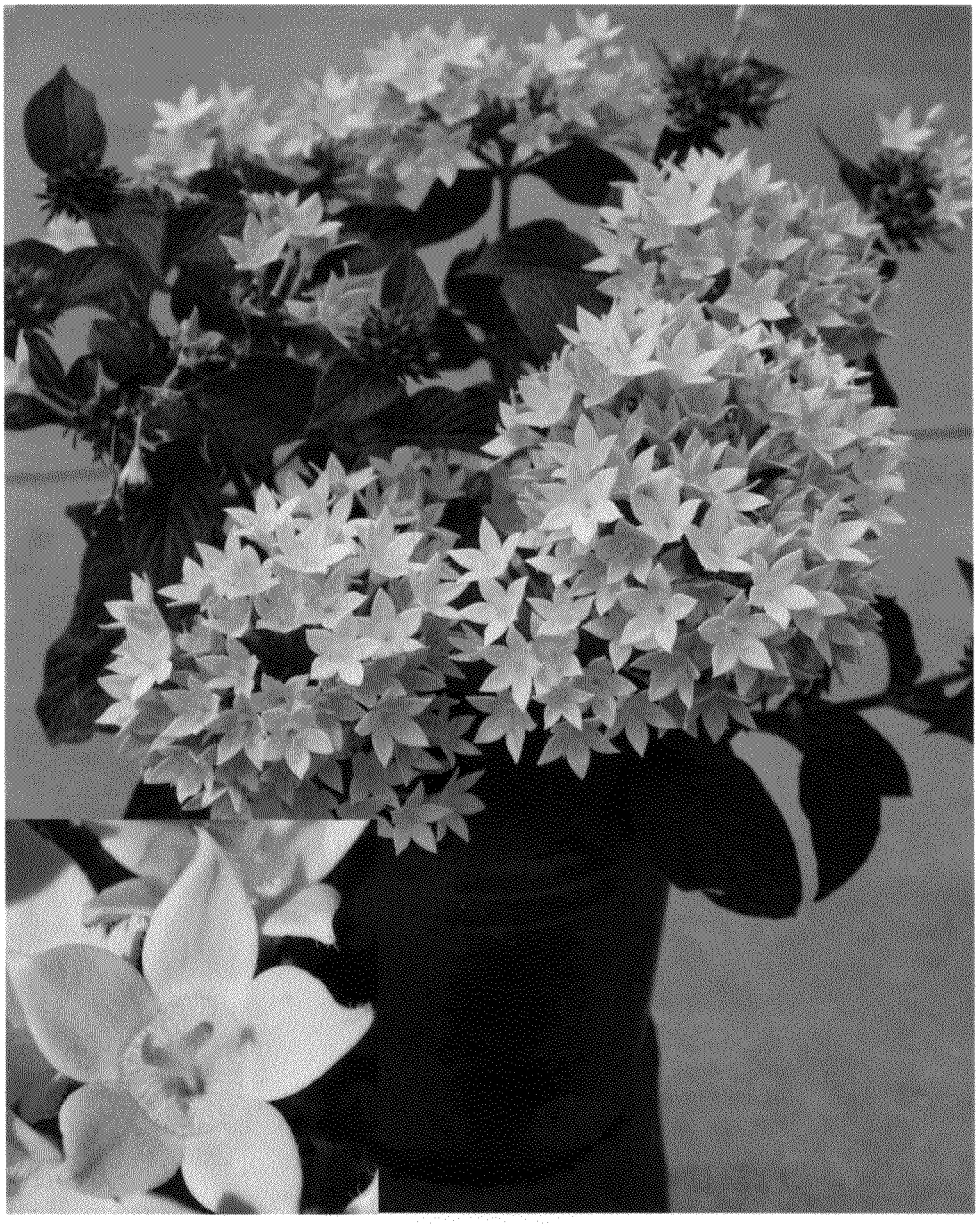

* * * * *